(12) United States Patent
Böttcher et al.

(10) Patent No.: US 6,624,303 B2
(45) Date of Patent: Sep. 23, 2003

(54) METHOD FOR PRODUCING N-ALKENYL AMIDES

(75) Inventors: Arnd Böttcher, Frankenthal (DE); Rolf Pinkos, Bad Dürkheim (DE); Thomas Preiss, Weisenheim am Sand (DE); Rudolf Erich Lorenz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/168,213

(22) PCT Filed: Dec. 12, 2000

(86) PCT No.: PCT/EP00/12578

§ 371 (c)(1), (2), (4) Date: Jun. 19, 2002

(87) PCT Pub. No.: WO01/46139

PCT Pub. Date: Jun. 28, 2001

(65) Prior Publication Data

US 2003/0028035 A1 Feb. 6, 2003

(30) Foreign Application Priority Data

Dec. 22, 1999 (DE) ......... 199 62 405

(51) Int. Cl.[7] ............. C07D 223/10
(52) U.S. Cl. ......... 540/485; 540/533; 540/604; 546/243; 548/543; 548/552
(58) Field of Search ......... 546/243; 548/543, 548/552; 540/604, 485, 533

(56) References Cited

U.S. PATENT DOCUMENTS 2,806,847 A  9/1957  Nedwick
4,410,726 A  10/1983 Parthasarathy et al.
5,665,889 A  9/1997  Chu et al.

FOREIGN PATENT DOCUMENTS

DE  1163 935   2/1964
DE  32 15093   1/1983

OTHER PUBLICATIONS

W. Reppe und Mitarbeiter, 135–183, Band 601, 1956.
JP Abst. 11060558—XP 002161138, 1999.

Primary Examiner—Shailendra Kumar
(74) Attorney, Agent, or Firm—Keil & Weinkauf

(57) ABSTRACT

A process for preparing N-alkenyl-amides by reacting the corresponding NH-amides with acetylenes in the liquid phase in the presence of basic alkali metal compounds and of a cocatalyst comprises using as the cocatalyst compounds of the general formulae (Ia) and/or (Ib)

$$R^1O\text{—}(CH_2CH_2CH_2CH_2O)_n\text{—}H \quad \text{(Ia):}$$

$$R^1O\text{—}(CH_2CH_2CH_2CH_2O)_n\text{—}R^2, \quad \text{(Ib):}$$

where n is 1, 2 or 3 and $R^1$ and $R^2$ are independently $C_1$- to $C_6$-alkyl or $C_2$- to $C_6$-alkenyl, or together a butenyl unit.

12 Claims, No Drawings

METHOD FOR PRODUCING N-ALKENYL AMIDES

This application is a 371 of PCT/EP00/2578, filed Dec. 12, 2000.

The present invention leads to an improved process for preparing N-alkenyl-amides by reacting the corresponding NH-amides with acetylenes in the liquid phase in the presence of basic alkali metal compounds and a cocatalyst.

N-Alkenyl-amides are used as monomers in the manufacture of plastics and paints. Polyvinylamides are used for example as laundry detergent assistants, as auxiliaries in cosmetic and medical products and also for stabilizing and clarifying beers and fruit juices. Polyvinyl-lactams, especially polyvinylpyrrolidone polymers, are widely used, for example as dispersants for pigments, as laundry detergent assistants, as auxiliaries in cosmetic and medical products and also as auxiliaries in textile processing and adhesive technology.

N-Alkenyl-lactams are produced on an industrial scale by reacting the corresponding NH-lactams with acetylenes in the presence of basic catalysts (see W. Reppe et al., Justus Liebigs Ann. Chem., 601 (1956) page 135–8 and DE-Auslegeschrift 1 163 835).

DE-Offenlegungsschrift 3 215 093 discloses a process for vinylating 2-pyrrolidone with ethyne in the presence of basic catalysts and in the additional presence of a polyoxyalkylene compound as cocatalyst. Useful polyoxyalkylene compounds are said to be crown ethers (eg 18-crown-6), polyoxyethylene, polyoxypropylene, selectively capped by alkyl or phenyl groups. Conversions up to 63% and selectivities around 90% are reported, the corresponding yield being not more 57%. The formation of polymeric residues is reduced. However, the cocatalysts mentioned are costly materials which are generally not recoverable, since they have high boiling points and therefore remain in the distillation bottoms together with the polymeric byproducts. In addition, they are not stable in the strongly basic medium of the reaction.

U.S. Pat. No. 5,665,889 describes a method for the production of N-vinyl-2-pyrrolidone from 2-pyrrolidone and ethyne in the presence of basic alkali metal compounds using cocatalysts comprising hydroxy end-capped ether oligomers, for example polytetrahydrofuran, or linear diols having at least 4 carbon atoms, for example, 1,4-butanediol. The vinylation takes place at a temperature ranging from 100 to 200° C., and at a pressure ranging from 7.5 to 30 atm (from 7.6 to 30 bar) in the course of a reaction time of several hours. The use of 1,4-butanediol produced a yield of only 77.2% even after a reaction time of 4 hours. The present inventors have determined that these cocatalysts, which have high boiling points, are generally impossible to separate from the polymeric byproducts or in the case of the use of 1,4-butanediol can be separated from the product of value only by means of inconvenient distillative or chemical methods.

It is an object of the present invention to develop a process for preparing N-alkenyl-amides that does not have the recited disadvantages, that permits yields of more than 80% and that makes the pure product obtainable in a simple manner.

We have found that this object is achieved by a process for preparing N-alkenyl-amides by reacting the corresponding NH-amides with acetylenes in the liquid phase in the presence of basic alkali metal compounds and of a cocatalyst, which comprises using as the cocatalyst compounds of the general formulae (Ia) and/or (Ib)

$R^1O—(CH_2CH_2CH_2CH_2O)_n—H$     (Ia):

$R^1O—(CH_2CH_2CH_2CH_2O)_n—R^2$,     (Ib):

where n is 1, 2 or 3 and $R^1$ and $R^2$ are independently $C_1$- to $C_6$-alkyl or $C_2$- to $C_6$-alkenyl, or together a butenyl unit.

The process of the invention provides N-alkenyl-amides in high selectivity and high yield from the corresponding NH amides and acetylenes in the presence of basic alkali metal compounds and of an inexpensive cocatalyst which is simple to remove again from the reaction mixture.

An essential feature of the process according to the invention is the presence of a cocatalyst (Ia) and/or (Ib)

$R^1O—(CH_2CH_2CH_2CH_2O)_n—H$     (Ia):

$R^1O—(CH_2CH_2CH_2CH_2O)_n—R^2$,     (Ib):

where n is 1, 2 or 3
and $R^1$ and $R^2$ are independently branched or unbranched $C_1$- to $C_6$-alkyl, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, or branched or unbranched $C_2$- to $C_6$-alkenyl having a double bond in any desired position, for example ethenyl (vinyl), 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-hexenyl, 2-hexenyl, 3-hexenyl, 4-hexenyl and 5-hexenyl, or $R^1$ and $R^2$ are together a butenyl unit, specifically $CH_2CH_2CH_2CH_2$, or mixtures thereof.

Examples of useful cocatalysts (Ia) and/or (Ib) for the process of the invention are 4-methoxy-1-butanol, 4-ethoxy-1-butanol, 4-propoxy-1-butanol, 4-butoxy-1-butanol, 1,4-dimethoxybutane, 1,4-diethoxybutane, 1,4-dipropoxybutane, 1,4-dibutoxybutane, 1-ethoxy-4-methoxybutane, 1-propoxy-4-methoxybutane, 1-butoxy-4-methoxybutane, 1-propoxy-4-ethoxybutane, 1-butoxy-4-ethoxybutane, 1-butoxy-4-propoxybutane, 4-vinyloxy-1-butanol, 4-(isopropenyloxy)-1-butanol, 4-propenyloxy-1-butanol, 1,4-divinyloxybutane, 1,4-bis(isopropenyloxy)butane, 1,4-bis(propenyloxy)butane, 1-vinyloxy-4-methoxybutane, 1-vinyloxy-4-ethoxybutane, 1-vinyloxy-4-propoxybutane, 1-(isopropenyloxy)-4-propoxybutane, 1-(propenyloxy)-4-propoxybutane, 4-(4'-methoxy-1'-butoxy)-1-butanol, 4-(4'-ethoxy-1'-butoxy)-1-butanol, 4-(4'-vinyloxy-1'-butoxy)-1-butanol, bis(4-methoxy-1-butyl) ether, bis(4-ethoxy-1-butyl) ether, bis(4-vinyloxy-1-butyl) ether, 10-crown-2, 15-crown-3 and 20-crown-4.

Preference is given to using cocatalysts of the formulae (Ia) and/or (Ib) where $R^1$ and $R^2$ are independently ethyl or vinyl, for example 4-ethoxy-1-butanol, 1,4-diethoxybutane, 4-vinyloxy-1-butanol, 1,4-divinyloxybutane, 1-vinyloxy-4-ethoxybutane, 4-(4'-ethoxy-1'-butoxy)-1-butanol, 4-(4'-vinyloxy-1'-butoxy)-1-butanol, bis(4-ethoxy-1-butyl) ether and bis(4-vinyloxy-1-butyl) ether or mixtures thereof.

Particular preference is given to using 4-ethoxy-1-butanol, 1,4-diethoxybutane, 4-vinyloxy-1-butanol, 1,4-divinyloxybutane, 1-vinyloxy-4-ethoxybutane or mixtures thereof. Very particular preference is given to using 1,4-diethoxy-butane, 1,4-divinyloxy-butane or mixtures thereof.

The cocatalysts to be used in the process of the invention are obtainable by the following syntheses:

(a) 4-Alkenyloxy-1-butanols and 1,4-dialkenyloxybutanes are formed by reacting 1,4-butanediol with acetylenes in the presence of a basic catalyst and separating the product by distillation. In this way it is possible for example to obtain 4-vinyloxy-1-butanol and 1,4-divinyloxybutane by reacting 1,4-butanediol with ethyne and distillative workup.

(b) 4-Alkoxy-1-butanols and 1,4-dialkoxybutanes are prepared by catalytic hydrogenation of the 4-alkenyloxy-1-butanols and 1,4-dialkenyloxybutanes obtained according to (a). Suitable hydrogenation catalysts are known to one skilled in the art. It is possible to use, for example, noble metal powders, mohr or black, supported hydrogenating metals, for example noble metals or copper on charcoal or oxidic carrier materials. 1,4-Diethoxybutane can thus be obtained by hydrogenating 1,4-divinyloxybutane.

Alternatively, the 4-alkoxy-1-butanols and 1,4-dialkoxybutanes are also obtainable by etherifying 1,4-butanediol with the corresponding alkanols according to etherification methods known to one skilled in the art.

(c) 1-Alkenyloxy-4-alkoxybutanes are obtained by reacting the 4-alkoxy-1-butanols obtained according to (b) with acetylenes according to (a).

(d) Alkoxy and alkenyloxy derivatives of dibutylene glycol and tributylene glycol are obtainable by intermolecular etherification of 1,4-butanediol and subsequent derivatization corresponding to (a) to (c).

(e) 1,4-Butanediol crown ethers are obtainable by intermolecular etherification of 1,4-butanediol.

The cocatalysts to be used in the process of the invention are easy to remove from the reaction mixture, especially from the N-alkenyl-amide products of value, compared with prior art cocatalysts. The greater the gap between the boiling points of the cocatalysts and those of the N-alkenyl-amides, whether in the direction of lower or higher boiling points, the simpler it is to remove the N-alkenyl-amides prepared. Generally the 1,4-dialkenyloxybutanes and 1,4-dialkoxybutanes have a distinctly lower boiling point than the N-alkenyl-amide products of value, so that the cocatalysts are removed by distillation before the products of value. In the case of the alkoxy and alkenyloxy derivatives of dibutylene glycol and of tributylene glycol and also the 1,4-butanediol crown ethers, by contrast, the boiling points of the N-alkenyl-amide products of value are generally lower, so that the higher molecular weight cocatalysts are removed by distillation after the products of value.

NH-amides useful as starting materials in the process of the invention include cyclic and noncyclic amides which contain the "—CO—NH—" unit in their charge-neutral form.

Useful noncyclic amides include for example the N-alkyl-amides of branched and unbranched, saturated and unsaturated $C_1$- to $C_{22}$-carboxylic acids, having branched and unbranched, saturated and unsaturated $C_1$- to $C_{10}$-alkyl groups on the amide nitrogen. Examples of noncyclic NH-amides are the methyl-, ethyl-, propyl-, 1-methylethyl-, butyl-, 1-methylpropyl-, 1,1-dimethylethyl-, pentyl-, hexyl, heptyl-, octyl-, nonyl- or decyl-amides of formic acid, acetic acid, propionic acid, butyric acid, valeric acid, isovaleric acid, pivalic acid, caproic acid, 2-ethylbutyric acid, enanthic acid, caprylic acid, 2-ethylhexanic acid, pelargonic acid, isononanoic acid, capric acid, neodecanoic acid, lauric acid, myristic acid, palmitic acid, stearic acid, oleic acid, linoleic acid, linolenic acid, arachidic acid and behenic acid. Preferred noncyclic NH-amides are N-methyl-acetamide, N-methyl-propionamide and N-ethyl-acetamide.

Particular preference is given to the use of cyclic NH-amides, which are known as NH-lactams. Useful NH-lactams for the process of the invention include 4- to 12-membered NH-lactams, for example 2-pyrrolidone, 2-piperidone, ε-caprolactam and alkyl derivatives thereof, for example 3-methyl-2-pyrrolidone, 4-methyl-2-pyrrolidone, 5-methyl-2-pyrrolidone, 3-ethyl-2-pyrrolidone, 3-propyl-2-pyrrolidone, 3-butyl-2-pyrrolidone, 3,3-dimethyl-2-pyrrolidone, 3,5-dimethyl-2-pyrrolidone, 5,5-dimethyl-2-pyrrolidone, 3,3,5-trimethyl-2-pyrrolidone, 5-methyl-5-ethyl-2-pyrrolidone, 3,4,5-trimethyl-2-pyrrolidone, 3-methyl-2-piperidone, 4-methyl-2-piperidone, 5-methyl-2-piperidone, 6-methyl-2-piperidone, 6-ethyl-2-piperidone, 3,5-dimethyl-2-piperidone, 4,4-dimethyl-2-piperidone, 3-methyl-ε-caprolactam, 4-methyl-ε-caprolactam, 5-methyl-ε-caprolactam, 6-methyl-ε-caprolactam, 7-methyl-ε-caprolactam, 3-ethyl-ε-caprolactam, 3-propyl-ε-caprolactam, 3-butyl-ε-caprolactam, 3,3-dimethyl-ε-caprolactam or 7,7-dimethyl-ε-caprolactam. Preference is given to using the unsubstituted 4- to 12-membered H-lactams

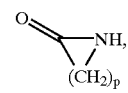

here p is from 2 to 10, for example β-propiolactam, 2-pyrrolidone (γ-butyrolactam), 2-piperidone (δ-valerolactam), ε-caprolactam and also alkyl-substituted derivatives thereof. Particular preference is given to the use of 2-pyrrolidone (γ-butyrolactam), 2-piperidone (δ-valerolactam) and ε-caprolactam.

Acetylenes used in the process of the invention are preferably unbranched and branched alkynes having 2 to 6 carbon atoms and a terminal triple bond, for example ethyne, propyne, 1-butyne, 1-pentyne, 1-hexyne. Particular preference is given to the use of ethyne and propyne, especially ethyne.

The cocatalyst to be used according to the invention is advantageously used in an amount of from 0.1 to 10% by weight, based on the NH-amide used. An amount of from 0.5 to 5% by weight is particularly preferred.

Basic alkali metal compounds useful as catalyst in the process of the invention include the oxides, hydroxides and/or alkoxides of lithium, sodium, potassium, rubidium and/or cesium and also mixtures thereof. Preferred alkoxides are compounds of low molecular weight alcohols, for example methoxide, ethoxide, propoxide, 1-methyl-ethoxide, butoxide, 1-methyl-propoxide, 2-methyl-propoxide and 1,1-dimethyl-ethoxide. Preference is given to using the oxides, hydroxides and/or alkoxides of sodium and/or potassium. Particular preference is given to sodium hydroxide and potassium hydroxide. The basic alkali metal compounds may be used as solids or solutions in water or alcohol. Preference is given to the use of solid, water- and alcohol-free alkali metal compounds. Mixtures of various alkali metal compounds are also possible.

The reaction with the acetylene may be carried out at a molar ratio of from 0.02 to 6.0%, preferably from 0.05 to 4.0%, between the total of basic alkali metal compounds used and the NH-amide.

The process of the invention may be carried out as follows:

The first step of the process according to the invention may be to dissolve the cocatalyst in the NH-amide. However, the addition may also take place later.

The next step is to contact the basic alkali metal compounds with the NH-amide. It may be pointed out that the NH-amide may at this point already include the requisite amount of cocatalyst. The alkali metal compound is added, for example, by dissolving it in the liquid NH-amide or by adding a solution of the alkali metal compounds to the NH-amide. It is also possible to dilute the NH-amide, or the solution of the alkali metal compound in the NH-amide, with a suitable solvent, for example in order to influence the reaction characteristics. Useful solvents dissolve both the NH-amide and the basic catalyst relatively readily and do not react chemically with the compounds used, ie have in particular no acidic centers which would scavenge the basic groups, and they are relatively easy to remove again, preferably by distillation, from the system after the synthesis of the N-alkenyl-amides. Examples of useful solvents are N-methylpyrrolidone, tetrahydrofuran or dialkyl ethers of glycols, di-, oligo- or polyglycols.

The solution of the basic alkali metal compounds in the NH-amide or its solutions is generally prepared according to customary methods by contacing the catalyst solid with the liquid by thorough mixing. This provides an accelerated dissolution of the solid and counteracts any local heating due to the heat of dissolution. Suitable apparatuses are known to those skilled in the art. Stirred tanks may be mentioned by way of example without limitation. The liquid is charged initially and the catalyst solid is added, if appropriate over a period of time, continuously or a little at a time with thorough mixing. When solutions of the basic alkali metal compounds in water or alcohols are used, the procedure is basically similar. Here too those skilled in the art would know of suitable methods. It is also possible to add the cocatalyst together with the alkali metal compound.

The solution of the basic alkali metal compounds in the NH-amide may be prepared not only in highly concentrated form as catalyst/NH-amide stock solution but also in low-concentrated form as catalyst/NH-amide reaction solution. The highly concentrated catalyst/NH-amide stock solution is set to a high catalyst concentration, which may be as high as the solubility limit, while the low-concentrated catalyst/NH-amide reaction solution is set to the catalyst concentration required for the reaction with acetylene. It will be appreciated that all stages in between are possible as well.

The reaction of the NH-amides with the alkali metal compounds byproduces water or alcohols in an equilibrium reaction in liquid form. Water or the alcohols formed remain in solution and, owing to the equilibrium relation, prevent complete conversion between the NH-amide and the basic alkali metal compounds. Specific removal of the water and/or alcohol of reaction formed results in a shift of the equilibrium in the direction of the alkali metal salt of the NH-amide, so that the salt mentioned may be obtained in sufficient concentration. The addition of the basic alkali metal compounds to the NH-amide may take place not only in a separate process step but also during the removal of the water/alcohol of reaction. In addition, the cocatalyst may be added in a separate step after addition of the alkali metal compound or before or during the removal of the water/alcohol of reaction.

The advantageous removal of the water and/or alcohol of reaction formed contributes to obtaining a particularly high selectivity to and yield of N-alkenyl-amides.

Particularly preferred methods for removing the water or low molecular weight alcohols of reaction are evaporation, binding to a suitable drier (adsorption) and removal through a suitable membrane. The methods mentioned may even be employed when aqueous or alcoholic catalyst solutions are used.

Evaporation exploits the large difference in vapor pressure between water/low molecular weight alcohol and the NH-amide. The water or alcohol of reaction is preferably evaporated at elevated temperature between 50 and 150° C. and a reduced pressure between 0.1 kPa (1 mbar abs) and a subatmospheric pressure. Evaporation may be effected in various ways. For example, it may be effected in a mixed vessel (eg stirred tank) by heating and/or applying a reduced pressure. Similarly, stripping with an inert gas, for example nitrogen, is possible. Evaporation may also be effected by passing the solution through an evaporator. Such equipment is described in the pertinent technical literature (see for example Ullmann's Encyclopedia of Industrial Chemistry, $6^{th}$ edition, 1998 Electronic Release, Chapter "Evaporation"). A particularly preferred method of evaporation is distillation. It may be carried out discontinuously, semicontinuously or continuously. In a discontinuous distillation, the NH-amide, the catalyst, which may be completely or else only partially dissolved, and, if appropriate, the cocatalyst are initially charged to the distillation flask and the temperature is raised and/or the pressure reduced to distill off the water or alcohol of reaction. In a semicontinuous distillation, for example, a solution of the catalyst in the NH-amide, which includes the cocatalyst, if appropriate, is fed to the column part and the water or alcohol of reaction is distilled off continuously. The water- or alcohol-free product collects in the distillation flask. A continuous distillation differs from a semicontinuous distillation mainly in that the water- or alcohol-free product is continuously removed from the bottom region. The distillations are preferably carried out at a pressure less than 0.1 MPa (1 bar abs).

The use of a drier exploits the exothermic adsorption of small molecules on suitable solids having large surface areas. A particularly important application is the removal of water. The technical literature describes a multiplicity of suitable driers (see for example Ullmann's Encyclopedia of Industrial Chemistry, $6^{th}$ edition, 1998 Electronic Release, Chapter "Zeolites"). Useful driers include for example, without limitation, zeolitic molecular sieves, for example the type 13X. The drying may also be effected in various ways. In one variant, for example, the drier is disposed directly in the reaction system in which the later reaction with the acetylene takes place. In another variant, the solution is passed through a bed of the drier and only subsequently introduced into the alkenylation reactor.

The third option mentioned, removal via a membrane, exploits the size difference between water or the low molecular weight alcohols and the teriary dialcohols. In one embodiment, the membrane is disposed directly in the reaction system in which the later reaction with the acetylene takes place. In another embodiment, the solution is passed over a membrane in an upstream apparatus. Suitable membranes are described in the pertinent technical literature (see for example Ullmann's Encyclopedia of Industrial Chemistry, $6^{th}$ edition, 1998 Electronic Release, Chapter "Membranes and Membrane Separation Processes").

The water and/or alcohol of reaction is preferably removed by the above-discussed methods of evaporation, adsorption and/or by a membrane. Any desired combinations between the individual methods are possible as well and may even be advantageous. Without limitation there may be mentioned a two-stage distillation, a distillation with downstream adsorption or a removal by means of a membrane with downstream adsorption. Particular preference is given to using distillative removal, which is most preferably carried out in a single stage, at a pressure of less than 0.1 MPa (1 bar abs).

The water or alcohol of reaction is advantageously removed to a residual level of less than 1% by weight, preferably less than 0.5% by weight, particularly preferably less than 0.2% by weight, based on the total amount of liquid.

The cocatalyst may also be added according to the invention after the removal of the water or alcohol of reaction. Care must be taken to ensure here that the cocatalyst feed is free of water and low molecular weight monoalcohols, for example methanol, ethanol or propanol, in order that the effect of the preceding stage is not diminished.

When the cocatalyst contains water or low molecular weight monoalcohols, these are to be removed before the cocatalyst is added. But in this case it is preferable to add the cocatalyst to the NH-amide/catalyst solution upstream of the process stage for removing the water or alcohol of reaction.

The reaction with the acetylene is effected by contacting the above-described, NH-amide-, catalyst- and cocatalyst-containing, beneficiated (ie water- and monoalcohol-free) solution with the acetylene in the liquid phase. The NH-amide/catalyst/cocatalyst solution may also have been diluted with a water- and monoalcohol-free solvent. Useful solvents generally include all solvents which are also useful in the solution of the NH-amide and of the basic catalysts. Examples of useful solvents are N-methylpyrrolidone, tetrahydrofuran or dialkyl ethers of glycols, di-, oligo- or polyglycols. The reaction is preferably carried out in undiluted form, ie without addition of a further solvent.

If a catalyst/NH-amide solution was prepared with a catalyst concentration above the level required for the reaction with acetylene, for example a catalyst/NH-amide stock solution, and treated according to the invention, it must now be diluted with further, water- and alcohol-free NH-amide. The diluting may take place both outside and inside the alkenylation reactor. The low-concentrated catalyst/NH-amide reaction solution treated according to the invention can be used directly.

The reaction with acetylene can be carried out in various ways. In the semicontinuous process, the entire NH-amide/catalyst/cocatalyst solution is initially charged and the acetylene metered in at the rate of reaction. The product solution is normally not removed until after the reaction has ended. In the continuous process, the NH-amide/catalyst/cocatalyst solution and the acetylene are introduced continuously and the corresponding product solution is removed continuously.

The alkenylation is generally carried out at from 100 to 200° C., preferably from 130 to 180° C., particularly preferably from 140 to 160° C. It is generally carried out at an acetylene pressure of less than 5 MPa (50 bar abs), preferably less than 3 MPa (30 bar abs), most preferably less than 2.4 MPa (24 bar abs). However, the total pressure of the system may be significantly higher, since the gas atmosphere above may for example additionally include inert gases, such as nitrogen or noble gases, which may be introduced by specific injection. So the total pressure in the system may easily be 20 MPa (200 bar abs) for example. If relatively high molecular weight acetylenes are used, then the autogenous acetylene presure will be very low and may for example be distinctly below 0.1 MPa (1 bar abs). Low molecular acetylenes, for example ethyne, propyne and 1-butyne, are generally set to an acetylene pressure of greater than 0.1 MPa (1 bar abs). This provides an economical space-time yield. An alkenylation with ethyne as the acetylene is preferably carried out at an acetylene (ethyne) pressure of from 0.5 to 3.0 MPa (5 to 30 bar abs), particularly preferably from 0.8 to 2.4 MPa (8 to 24 bar abs), most preferably from 1.6 to 2.0 MPa (16 to 20 bar abs).

The reactor used for the alkenylation may in principle be any apparatus described for gas-liquid reactions in the pertinent technical literature. A high space-time yield requires thorough mixing between the NH-amide/catalyst/cocatalyst solution and the acetylene. Nonlimiting examples are stirred tanks, stirred tank batteries, flow tubes (preferably with internal fitments), bubble columns and loop reactors. The reactor effluent is worked up according to known methods. Preference is given to a distillation into a plurality of fractions. Distillations are preferably carried out at a pressure less than 0.1 MPa (1 bar abs). It is particularly preferable to recover not only the N-alkenyl-amide but also the cocatalysts as a fraction. Depending on the choice of cocatalysts to be used according to the invention, they are separated off in a lower boiling or higher boiling fraction before or after the N-alkenyl-amide. Various fractions may be mentioned without limitation: cocatalyst (before or after N-alkenyl-amide), N-alkenyl-amide, unconverted NH-amide, various intermediate boilers, low boilers and high boilers. According to intention, these may be recovered as crude fraction or in high purity. It is also possible to combine some fractions. The distillation may be carried out continuously, semicontinuously or discontinuously. In addition, it may be carried out in one column, with or without sidestream takeoffs, as well as in a plurality of consecutive columns. Suitable methods will be known to those skilled in the art. The process of the invention, as described, is a simple way of obtaining N-alkenyl-amide in a purity of above 99.8%.

The optionally removed unconverted NH-amide may be recycled in the process of the invention without further purification measures. For this, it is not necessary to recover the starting material in high purity, so that a crude-distilled fraction may be used as well. However, it is advantageous to remove those products having a distinctly higher boiling point.

The process of the invention allows, usually advantageously, the removed cocatalysts to be recycled. It is not necessary to recover them in high purity, so that a crude-distilled fraction may be used as well. However, it is advantageous to remove those products having a distinctly higher boiling point. Any losses of cocatalysts are to be made good by addition of virgin cocatalysts.

The process of the invention is particularly preferable for preparing

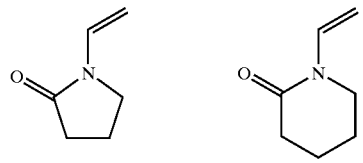

N-vinyl-2-pyrrolidone   N-vinyl-2-piperidone (N-Vinyl-γ-butyrolactam)   (N-Vinyl-δ-valerolactam)

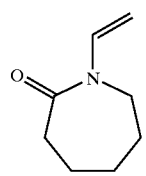

N-vinyl-ε-caprolactam and mixtures thereof. Starting materials for this are the corresponding NH-lactams 2-pyrrolidone (γ-butyrolactam), 2-piperidone (δ-valerolactam) and ε-caprolactam. The preparation of N-vinyl-ε-caprolactam is very particularly preferred.

In a general embodiment, the basic alkali metal compound (catalyst) and the cocatalyst are added a little at a time into the liquid, optionally solvent-diluted, NH-amide and mixed in. The resulting solution is then passed over a zeolitic drier into a stirred tank. The presence of the drier removes the water of reaction. The then almost anhydrous solution has the acetylene passed into it with thorough mixing at from 100 to 200° C. The preferred ethyne is preferably introduced up to a pressure of 2.4 MPa (24 bar abs). Consumed acetylene is replenished. After the absorption of acetylene has ceased, the reaction system is depressurized. The reaction solution is transferred into a distillation column and the N-alkenyl-amide is isolated overhead in high purity after removal of the lower boiling components.

In a further general embodiment, a mixing vessel is used to prepare an almost concentrated solution (ie about 80% of maximum solubility) of the basic alkali metal compound in the NH-amide. This solution is continuously fed to a vacuum distillation column and the water of reaction formed is taken off overhead. The water-free catalyst/NH-amide solution is continuously removed from the bottom region and admixed with further anhydrous NH-amide and with anhydrous cocatalyst. The recycling streams are also fed in at this point. The reactant mixture is then fed into a continuous loop reactor where the reaction with the acetylene is carried out at from 100 to 200° C. The preferred ethyne is preferably introduced up to a pressure of 2.4 MPa (24 bar abs). The reaction solution is continuously removed from the loop reactor and worked up by distillation. The N-alkenyl-amide is isolated as pure product. Recovered unconverted NH-amide and removed alkenylated cocatalyst are recycled.

In a third, particularly preferred embodiment, a mixing vessel is used to prepare a solution of about 2% by weight of potassium hydroxide in ε-caprolactam and admixed with about 1.0% by weight of 1,4-diethoxybutane and/or 1,4-divinyloxybutane. This solution is continuously fed to a vacuum distillation column and the water of reaction formed is taken off overhead. The almost anhydrous solution is continuously removed from the bottom region into a stirred tank where the semicontinuous reaction takes place with the gaseous ethyne at from 140 to 160° C. and from 1.5 to 2.0 MPa (15 bis 20 bar abs). After the reaction has ended, the reactor contents are removed from the reactor into a distillative workup stage where they are separated into low boilers, comprising 1,4-diethoxybutane and/or 1,4-divinyloxybutane, N-vinyl-ε-caprolactam and high boilers. The N-vinyl-ε-caprolactam is recovered in high purity.

The process of the invention provides a simple way of obtaining N-alkenyl-amides in very high yield and purity by reacting the corresponding NH-amides with acetylenes in the presence of basic alkali metal compounds and of a cocatalyst. The outstanding advantages over the prior art are in particular:

- The use of a cocatalyst which is, in the case of the particularly preferred 1,4-diethoxybutane or 1,4-divinyloxybutane, very inexpensive.
- The ease of removal of the N-alkenyl-lactam from the reaction solution and the very high purity attainable thereby.
- The possibility to recover and reuse the cocatalyst.

EXAMPLES

Definitions

The conversion, selectivity and yield reported in the description and the examples are defined by the following equations:

Conversion=$[m_{before}$(NH-amide)$-m_{after}$(NH-amide)$]/m_{before}$(NH-amide)

Selectivity=$m_{after}$(N-alkenyl-amide)$/[m_{before}$(NH-amide)$-m_{after}$(NH-amide)$]$ Yield=Conversion×selectivity=$m_{after}$(N-alkenyl-amide)$/m_{before}$(NH-amide).

where:

| | |
|---|---|
| $m_{before}$(NH-amide) is | the mass of NH-amide used |
| $m_{after}$(NH-amide) is | the unconverted mass of NH-amide |
| $m_{after}$(N-alkenyl-amide) | is the mass of N-alkenyl-amide formed, after purifying distillation. |

Procedure 100 g of ε-caprolactam were admixed with 2.5 g of KOH in each case and dissolved with stirring. Then the water of reaction was removed at 0.1 kPa (1 mbar abs) and 100° C. The almost anhydrous reaction batch was then optionally admixed with cocatalyst, introduced into an autoclave and pressurized with nitrogen to 0.2 MPa (2 bar abs) at room temperature. After heating to 90° C., ethyne was injected to 1.2 MPa (12 bar abs). Ethyne consumed by the reaction was replenished by continuous injection to 1.2 MPa (12 bar abs). After 12 hours the run was discontinued and the reaction product distilled. Analysis was by gas chromatography.

Example 1

Comparative Example Without Cocatalyst

Example 1 was carried out without addition of a cocatalyst. The amount of ethyne taken up was 0.69 mol per mole of ε-caprolactam. The distillative workup yielded N-vinyl-ε-caprolactam in a yield of 77.9%. A viscid distillation residue was obtained.

Example 2

Inventive

Example 2 was carried out by adding 1% by weight of 1,4-diethoxybutane as cocatalyst. The amount of ethyne taken up was 0.87 mol per mole of ε-caprolactam. The distillative workup yielded N-vinyl-ε-caprolactam in a yield of 81.9%. A liquid distillation residue was obtained.

Example 3

Inventive

Example 3 was carried out by adding 1% by weight of 1,4-divinyloxybutane as cocatalyst. The amount of ethyne taken up was 0.97 mol per mole of ε-caprolactam. The distillative workup yielded N-vinyl-ε-caprolactam in a yield of 85.0%. A liquid distillation residue was obtained.

A summary of the examples is reported in Table 1. The lowest yield of 77.9% was obtained without cocatalyst, under otherwise identical conditions. The two examples with cocatalyst gave a distinctly higher yield between 81.9 and 85.0%. The positive effect of the cocatalysts resulted in the formation of fewer byproducts, which manifested itself in the consistency of the distillation residue.

TABLE 1

| No. | Cocatalyst | Relative takeup of ethyne [mol/mole] | Conversion [%] | Selectivity [%] | Yield [%] | Distillation residue | Consistency of residue |
|---|---|---|---|---|---|---|---|
| 1 | without (comparative example) | 0.69 | 86.1 | 90.5 | 77.9 | 8.2 | viscid |
| 2 | 1% by weight of 1,4-diethoxybutane | 0.87 | 93.7 | 87.4 | 81.9 | 11.8 | liquid |
| 3 | 1% by weight of 1,4-divinyloxybutane | 0.97 | 96.3 | 88.3 | 85.0 | 11.3 | liquid |

We claim:

1. A process for preparing N-alkenyl-amides by reacting the corresponding NH-amides with acetylenes in the liquid phase in the presence of basic alkali metal compounds and of a cocatalyst, which comprises using as the cocatalyst compounds of the general formulae (Ia) and/or (Ib)

$$R^1O-(CH_2CH_2CH_2CH_2O)_n-H \quad (Ia):$$

$$R^1O-(CH_2CH_2CH_2CH_2O)_n-R^2, \quad (Ib):$$

where n is 1, 2 or 3 and $R^1$ and $R^2$ are independently $C_1$- to $C_6$-alkyl or $C_2$- to $C_6$-alkenyl, or together a butenyl unit.

2. A process as claimed in claim 1, wherein the cocatalyst used comprises compounds of the formulae (Ia) and/or (Ib) where $R^1$ and $R^2$ are independently ethyl or vinyl.

3. A process as claimed in claim 1, wherein the cocatalyst used is 1,4-diethoxybutane or 1,4-divinyloxybutane.

4. A process as claimed in claim 1, wherein said cocatalyst (Ia) and/or (Ib) is used in an amount of from 0.1 to 10% by weight, based on the NH-amide used.

5. A process as claimed in claim 1, wherein the basic alkali metal compounds used are sodium hydroxide and/or potassium hydroxide.

6. A process as claimed in claim 1, wherein the basic alkali metal compounds are used in a molar amount of from 0.05 to 4.0% of the molar amount of the NH-amide used.

7. A process as claimed in claim 1, wherein the water and/or alcohol of reaction formed in the course of the reaction between the basic alkali metal compounds and the NH-amide is removed from the system by evaporation, by adsorption and/or by a membrane.

8. A process as claimed in claim 1, wherein the water and/or alcohol of reaction formed is removed from the system by distillation.

9. A process as claimed in claim 1, wherein the reaction between the NH-amides and the acetylenes is carried out at from 100 to 200° C. and at an acetylene pressure of less than 5 MPa.

10. A process as claimed in claim 1, wherein the cocatalyst is recovered and reused as cocatalyst.

11. A process as claimed in claim 1, wherein the N-alkenyl-amides prepared are N-alkenyl-lactams.

12. A process as claimed in claim 11, wherein the N-alkenyl-lactams prepared are N-vinyl-2-pyrrolidone, N-vinyl-2-piperidone and/or N-vinyl-ε-caprolactam.

* * * * *

UNITED STATES PATENT AND TRADEMARK OFFICE
CERTIFICATE OF CORRECTION

PATENT NO. : 6,624,303 B2  
DATED : September 23, 2003  
INVENTOR(S) : Boettcher et al.

It is certified that error appears in the above-identified patent and that said Letters Patent is hereby corrected as shown below:

<u>Column 2,</u>
Lines 2 and 35, "butenyl" should be -- butylen --.

<u>Column 11,</u>
Line 27, "butenyl" should be -- butylen --.

Signed and Sealed this

Thirtieth Day of March, 2004

JON W. DUDAS
*Acting Director of the United States Patent and Trademark Office*